United States Patent
Mo

[19]

[11] Patent Number: 6,123,670
[45] Date of Patent: Sep. 26, 2000

[54] ULTRASOUND IMAGING WITH OPTIMAL IMAGE QUALITY IN REGION OF INTEREST

[75] Inventor: Larry Y. L. Mo, Waukesha, Wis.

[73] Assignee: General Electric Company, Milwaukee, Wis.

[21] Appl. No.: 09/211,910

[22] Filed: Dec. 15, 1998

[51] Int. Cl.[7] ...................................................... A61B 8/00
[52] U.S. Cl. ........................................................ 600/447
[58] Field of Search .................................. 600/437, 440, 600/441, 443, 447; 73/609, 617, 625–626; 128/916

[56] References Cited

U.S. PATENT DOCUMENTS

| | | | |
|---|---|---|---|
| 5,379,642 | 1/1995 | Reckwerdt et al. | 73/625 |
| 5,873,830 | 2/1999 | Hossack et al. | 600/447 |
| 5,967,985 | 10/1999 | Hayakawa | 600/440 |
| 5,984,869 | 11/1999 | Chiao et al. | 600/437 |

*Primary Examiner*—Marvin M. Lateef
*Assistant Examiner*—Ali M. Imam
*Attorney, Agent, or Firm*—Dennis M. Flaherty; Christian G. Cabou; Phyllis Y. Price

[57] ABSTRACT

A method and an apparatus for displaying an ultrasound image comprising a region of interest (ROI) having an optimal image quality and a background region having a normal image quality. In the displayed image the background region lies outside the ROI. The optimal image quality within the ROI is achieved by using a set of imaging parameters which are different than the set of imaging parameters used to acquire the background image, including one or more of the following: different (e.g., shorter) transmit waveforms, an increased number of transmit focal zones per unit depth, different transmit and/or receive apertures, different center frequencies for the receive bandpass filter (primary and/or (sub)harmonics), and higher vector density (i.e., decreased vector spacing). Since the optimal imaging is restricted to a ROI, a high frame rate is still possible within the ROI depending on its size.

21 Claims, 4 Drawing Sheets

ULTRASOUND IMAGING WITH OPTIMAL IMAGE QUALITY IN REGION OF INTEREST

FIELD OF THE INVENTION

This invention generally relates to B-mode imaging of biological tissues. In particular, the invention relates to methods for optimizing resolution of a B-mode ultrasound image while maintaining a high frame rate.

BACKGROUND OF THE INVENTION

Conventional ultrasound imaging systems comprise an array of ultrasonic transducer elements arranged in one or more rows and driven with separate voltages. By selecting the time delay (or phase) and amplitude of the applied voltages, the individual transducer elements in a given row can be controlled to produce ultrasonic waves which combine to form a net ultrasonic wave that travels along a preferred vector direction and is focused at a selected point along the beam. The beamforming parameters of each of the firings may be varied to provide a change in maximum focus or otherwise change the content of the received data for each firing, e.g., by transmitting successive beams along the same scan line with the focal point of each beam being shifted relative to the focal point of the previous beam. In the case of a steered array, by changing the time delays and amplitudes of the applied voltages, the beam with its focal point can be moved in a plane to scan the object. In the case of a linear array, a focused beam directed normal to the array is scanned across the object by translating the aperture across the array from one firing to the next.

The same principles apply when the transducer probe is employed to receive the reflected sound in a receive mode. The voltages produced at the receiving transducer elements are summed so that the net signal is indicative of the ultrasound reflected from a single focal point in the object. As with the transmission mode, this focused reception of the ultrasonic energy is achieved by imparting separate time delay (and/or phase shifts) and gains to the signal from each receiving transducer element.

A single scan line (or small localized group of scan lines) is acquired by transmitting focused ultrasound energy at a point in the region of interest, and then receiving the reflected energy over time. The focused transmit energy is referred to as a transmit beam. During the time after transmit, one or more receive beamformers coherently sum the energy received by each channel, with dynamically changing phase rotation or delays, to produce peak sensitivity along the desired scan lines at ranges proportional to the elapsed time. The resulting focused sensitivity pattern is referred to as a receive beam. A scan line's resolution is a result of the directivity of the associated transmit and receive beam pair.

A B-mode ultrasound image is composed of multiple image scan lines. The brightness of a pixel is based on the intensity of the echo return from the biological tissue being scanned. The outputs of the receive beamformer channels are coherently summed to form a respective pixel intensity value for each sample volume in the object region or volume of interest. These pixel intensity values are log-compressed, scan-converted and then displayed as a B-mode image of the anatomy being scanned.

In conventional B-mode imaging, image quality is determined largely by the point resolution which can be characterized by the point spread function (PSF) of the imager. The axial profile of the PSF can be sharpened by using short transmit bursts (higher frequency or fewer cycles) and/or pre-skewing of the transmit waveform to counteract tissue attenuation effects. The lateral dimension of the PSF can be reduced by using lower F-number (focal length to aperture ratio) and/or higher transmit frequency. In addition, all three dimensions of the PSF can be sharpened by using the second (or higher) harmonic frequency band on receive to form the image.

An increased lateral resolution, however, is often achieved at the expense of the acoustic frame rate for two reasons. First, the larger lateral spatial bandwidth (narrower PSF) must be accompanied by an appropriate increase in vector density (decrease in vector spacing) in order to satisfy spatial sampling requirements. Otherwise the expected improvements in lateral resolution will not actually be realized; instead, distracting lateral spatial aliasing artifacts may show up in the B-mode image. In non-zoom mode, increasing the vector density will generally compromise frame rate. Second, if the lateral resolution in the focal region is achieved by using lower F-numbers (larger apertures), the depth of field (axial length of the focal region) will be reduced. This means that more focal zones must be used in order to maintain acceptable image uniformity from the near field to the far field. Increasing the number of focal zones will also reduce the frame rate.

For live scanning of moving body parts, the acoustic frame rate must be maintained at some minimum acceptable level. Therefore, in practice, frame rate requirements tend to limit the maximum allowable vector density and number of focal zones, which in turn may limit the maximum aperture size and resolution that the system is capable of supporting. In prior art imagers, maximum resolution and high frame rates cannot generally be achieved simultaneously, except in zoom mode or by reducing the image wedge size to a very small area.

SUMMARY OF THE INVENTION

The present invention is a method and an apparatus for displaying an ultrasound image comprising a region of interest (ROI) having an optimal image quality and a background region having a less than optimal (hereinafter "normal") image quality. As used herein, the term "optimal image quality" includes high/maximum resolution and/or high frame rate, which, as discussed above, are often traded off against each other in conventional imagers.

In accordance with the preferred embodiments of the invention, the displayed image has a ROI and a background region which lies outside and is contiguous with the ROI. The optimal image quality within the ROI is achieved by using a set of imaging parameters which are different than the set of imaging parameters used to acquire the image data in the background region. The different imaging parameters of the ROI as compared to the background region may include, e.g., different (e.g., shorter) transmit waveforms, an increased number of transmit focal zones per unit depth, different transmit and/or receive apertures, different center frequencies for the receive bandpass filter (primary and/or (sub)harmonics), and higher vector density (i.e., decreased vector spacing). Since the optimal imaging is restricted to a ROI, a high frame rate is still possible within the ROI depending on its size. Hence, optimal imaging within a ROI can overcome the fundamental tradeoff between resolution and frame rate. The background image (outside the ROI) is to be maintained at or above some minimum acceptable level in terms of resolution and/or frame rate, and is still important for providing the "big picture" surrounding the special ROI or "small picture." It should be apparent that this new "picture in a picture" imaging mode can be applied to linear, curvilinear and sector scans.

The B-mode "picture in a picture" feature in accordance with the invention will be useful in many clinical scanning situations where the sonographer needs to examine a suspected diseased region with the highest possible resolution and/or frame rate. In conventional systems, a zoom mode is available for detailed examination of a ROI, but the conventional zoom mode enlarges the ROI to fill the entire image display, and does not provide the surrounding big picture, which may be important for proper interpretation of the small picture. Also, the "picture in a picture" mode enables the user to move the optimal image quality ROI freely within the big picture, which may prove very useful in searching diseased areas.

The "picture in a picture" mode can also be used in conjunction with advanced B-mode imaging techniques such as wideband imaging ("delta function" transmit waveform), tissue harmonic imaging and coded excitation, in which the main image quality benefit is seen only in the near field (for ultra-wideband transmit), mid-field (for tissue harmonics) or far field (for coded excitation). The availability of a ROI image within the full image will enable such advanced imaging techniques to be applied only over the region(s) of benefit, while allowing regular imaging for the remainder of the image. The use of a distinct optimal image quality ROI will also alleviate the need for matching the gains and texture of different focal zones associated with different transmit waveforms.

DETAILED DESCRIPTION OF THE PREFERRED EMBODIMENTS

Figure 1:
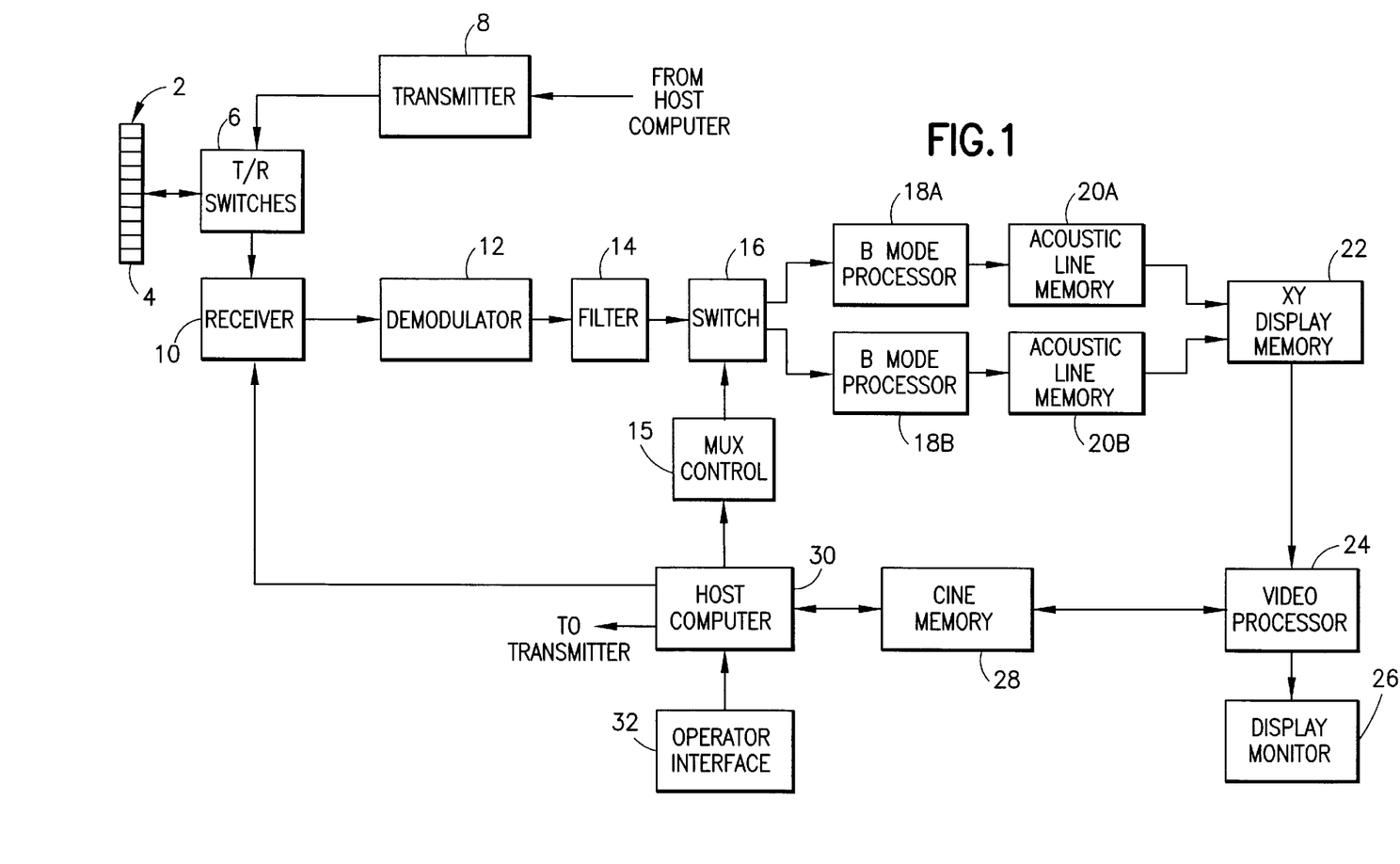
FIG. 1 is a block diagram showing an ultrasound imaging system in accordance with one preferred embodiment of the invention.

An ultrasound imaging system in accordance with one preferred embodiment of the invention is generally depicted in FIG. 1. The system comprises a transducer array 2 consisting of a plurality of separately driven transducer elements 4, each of which produces a burst of ultrasonic energy when energized by a respective pulsed waveform produced by a transmitter 8. The ultrasonic energy reflected back to transducer array 2 from the object under study is converted to an electrical signal by each receiving transducer element 4 and applied separately to a receiver 10 through a set of transmit/receive (T/R) switches 6. The T/R switches 6 are typically diodes which protect the receive electronics from the high voltages generated by the transmit electronics. The transmit signal causes the diodes to shut off or limit the signal to the receiver 10. The transmitter and receiver each comprise beamformers which are operated under control of a host computer (i.e., master controller) 30. A complete scan is performed by acquiring a series of echoes in which transmitter 8 is gated ON momentarily to energize each transducer element 4 in the transmit aperture, and the subsequent echo signals produced by each transducer element are applied to receiver 10. The receiver 10 combines the separate echo signals from each transducer element to produce a single echo signal which is used to produce a line in an image on a display monitor 26.

In accordance with one preferred embodiment of the invention, the transmit and receive beamformers are programmed by the host computer to acquire a first set of acoustic data corresponding to an optimal ROI image and a second set of acoustic data corresponding to a normal background image. In particular, for optimal imaging, the transmit beamformer transmits ultrasound beams having a first vector density and a first number of transmit focal zones per unit depth in the ROI, while for normal imaging, the transmit beamformer transmits ultrasound beams having a second vector density in the sector overlapped by the ROI and a second number of transmit focal zones per unit depth in the depth range corresponding to the ROI depth range. In accordance with one preferred embodiment, the first number of transmit focal zones per unit depth is greater than or equal to the second number of transmit focal zones per unit depth, i.e., the axial length of the transmit focal zones for optimal imaging is less than the transmit focal zone axial length for normal imaging. This is accomplished by using a wider transmit aperture for optimal imaging. Optionally, in addition to the first number of transmit focal zones per unit depth being greater than the second number of transmit focal zones per unit depth, the first vector density is equal to or greater than the second vector density. (For normal imaging, the transmit beamformer also transmits ultrasound beams in sectors not overlapped by the ROI and transmits ultrasound beams at depths outside the ROI depth range. The vector density in sectors not overlapped by the ROI may be less than the second vector density, while the number of transmit focal zones per unit depth at depths outside the ROI depth range may be less than the second number of transmit focal zones per unit depth.) The result will be a ROI image which has higher resolution.

Alternatively, the number of transmit focal zones, the vector spacing and the transmit aperture width can be the same for optimal and normal imaging, but the frame rate is maintained at a higher rate for the optimal imaging. This is accomplished by scanning the ROI at a first rate and scanning the background region at a second rate less than the first rate, each ROI scan consisting of a set of transmit beams focused in the ROI and each background scan consisting of a set of transmit beams focused in the background region. Preferably, the transmit beams for optimal and normal imaging are interleaved.

The receiver's signal inputs are the low-level analog RF signals from the transducer elements. The receiver is responsible for analog-to-digital conversion and for receive beamforming. In baseband imaging systems, the beamsummed signal is output to a demodulator 12, which converts the beamsummed signal into baseband in-phase I and quadrature Q receive beams. The I and Q acoustic data vectors from the demodulator 12 are output to an FIR filter 14, which is programmed with filter coefficients from a filter coefficient memory (not shown). The filter coefficient memory is programmed by the host computer.

The acoustic data from filter 14 is sent to a switch 16. In a first switch state, acoustic data vectors acquired during normal scanning are output to a B-mode processor 18A. In a second switch state, acoustic data vectors acquired during optimal scanning are output to a second B-mode processor 18B. As previously mentioned, the acoustic data vectors for optimal and normal imaging can be interleaved in a manner to maintain a higher frame rate for the optimal imaging. If the frame rates for optimal and normal imaging are the same, the acoustic data vectors for one optimal image frame can be acquired and then the acoustic data vectors for one normal image frame can be acquired, or the respective acoustic data vectors can be interleaved. The state of switch 16 is controlled by a multiplexer control 15, which is in turn controlled by the host computer 30.

In accordance with one preferred embodiment, for both normal and optimal imaging, the demodulator 12 and FIR filter 14 are programmed to convert a band of frequencies centered at the fundamental frequency $f_0$ of the transmit waveform into baseband I/Q data. In accordance with another preferred embodiment, for normal imaging the demodulator 12 and filter 14 are respectively programmed with a first demodulation frequency and a first set of filter coefficients to convert a band of frequencies centered at the fundamental frequency $f_0$ of the transmit waveform into I/Q data, while for optimal imaging they are programmed with a second demodulation frequency and a second set of filter coefficients to convert a band of frequencies centered at a harmonic frequency $kf_0$ or at a subharmonic frequency $f_0/k$ (where k is a positive integer greater than unity) into I/Q data.

Depending on whether the acoustic data is for the background image or the optimal ROI, the output of filter 14 is channeled to the appropriate B-mode processor. The B-mode processors 18A and 18B convert the respective streams of I and Q acoustic data into log-compressed versions of the respective signal envelopes. Each B-mode processor outputs the time-varying amplitude of the envelope of the signal input thereto. The envelope of a baseband signal is the magnitude of the vector which I and Q represent. The I,Q phase angle is not used in the B-mode display.

The magnitude (i.e., intensity) of the signal is the square root of the sum of the squares of the orthogonal components, i.e., $(I^2+Q^2)^{1/2}$.

The B-mode intensity data is output to a scan converter comprising respective B-mode acoustic line memories 20A and 20B followed by an X-Y display memory 22. Separate acoustic line memories are provided because the acoustic frame rates for the optimal and normal imaging can be very different. The acoustic line memory 20A accepts the processed vectors of B-mode intensity data acquired during scanning of the background area and interpolates where necessary. Similarly, the acoustic line memory 20B accepts the processed vectors of B-mode intensity data acquired during scanning of the ROI and interpolates where necessary. Each acoustic line memory also performs the coordinate transformation of the B-mode intensity data from polar coordinate (R-θ) sector format or Cartesian coordinate linear format to appropriately scaled Cartesian coordinate display pixel intensity data. The optimal-image-quality pixel intensity data for the ROI and the normal-image-quality pixel intensity data for the contiguous background region outside the ROI are both written into the X-Y display memory 22. In the case where the acoustic data stored in acoustic line memory 20A includes data derived from the region of interest during normal imaging, the optimal-image-quality data acquired from the ROI is stored instead of the normal-image-quality data acquired from the ROI.

The scan-converted "picture in a picture" frame is passed to a video processor 24, which converts the pixel intensity data from display memory 22 to the video frame rate and then maps the pixel intensity data to a gray-scale mapping for video display. A conventional ultrasound imaging system typically employs a variety of gray maps, which are simple transfer functions of the raw intensity data to display gray-scale levels. The gray-scale image frames are then sent to the display monitor 26 for display.

The B-mode images displayed by monitor 26 are produced from an image frame of data in which each datum indicates the intensity or brightness of a respective pixel in the display. An image frame may, e.g., comprise a 256×256 data array in which each display pixel intensity datum is an 8-bit binary number that indicates pixel brightness. Each pixel has an intensity value which is a function of the backscatter cross section of a respective sample volume in response to interrogating ultrasonic pulses and the gray map employed. The displayed image represents the tissue and/or blood flow in a scan plane through the body being imaged.

In accordance with the preferred embodiment of the present invention, the location and size of the region of interest can be selected via the operator interface.

Before gray mapping, successive frames of display pixel intensity data in the video processor 24 are stored in a cine memory 28 on a first-in, first-out basis. Storage can be continuous or as a result of an external trigger event. The cine memory 28 is like a circular image buffer that runs in the background, capturing image data that is displayed in real time to the user. When the user freezes the system (by operation of an appropriate device on the operator interface 32), the user has the capability to view image data previously captured in cine memory.

System control is centered in host computer 30, which accepts operator inputs through the operator interface 32 (e.g., a control panel) and in turn controls the various subsystems. The host computer 30 performs system level control functions. A system control bus (not shown) provides the interface from the host computer to the subsystems. The host computer preferably incorporates a scan controller (not shown) which provides real-time (acoustic vector rate) control inputs to the various subsystems. The scan controller is programmed by the host computer CPU with the vector sequences and synchronization options for acoustic frame acquisitions. Thus, the scan controller controls the beam distribution and the beam density. The scan controller transmits the beam parameters defined by the host computer CPU to the subsystems via a scan control bus (not shown). Alternatively, the scan controller can be a separate dedicated processor programmed by the host computer.

Figure 2:
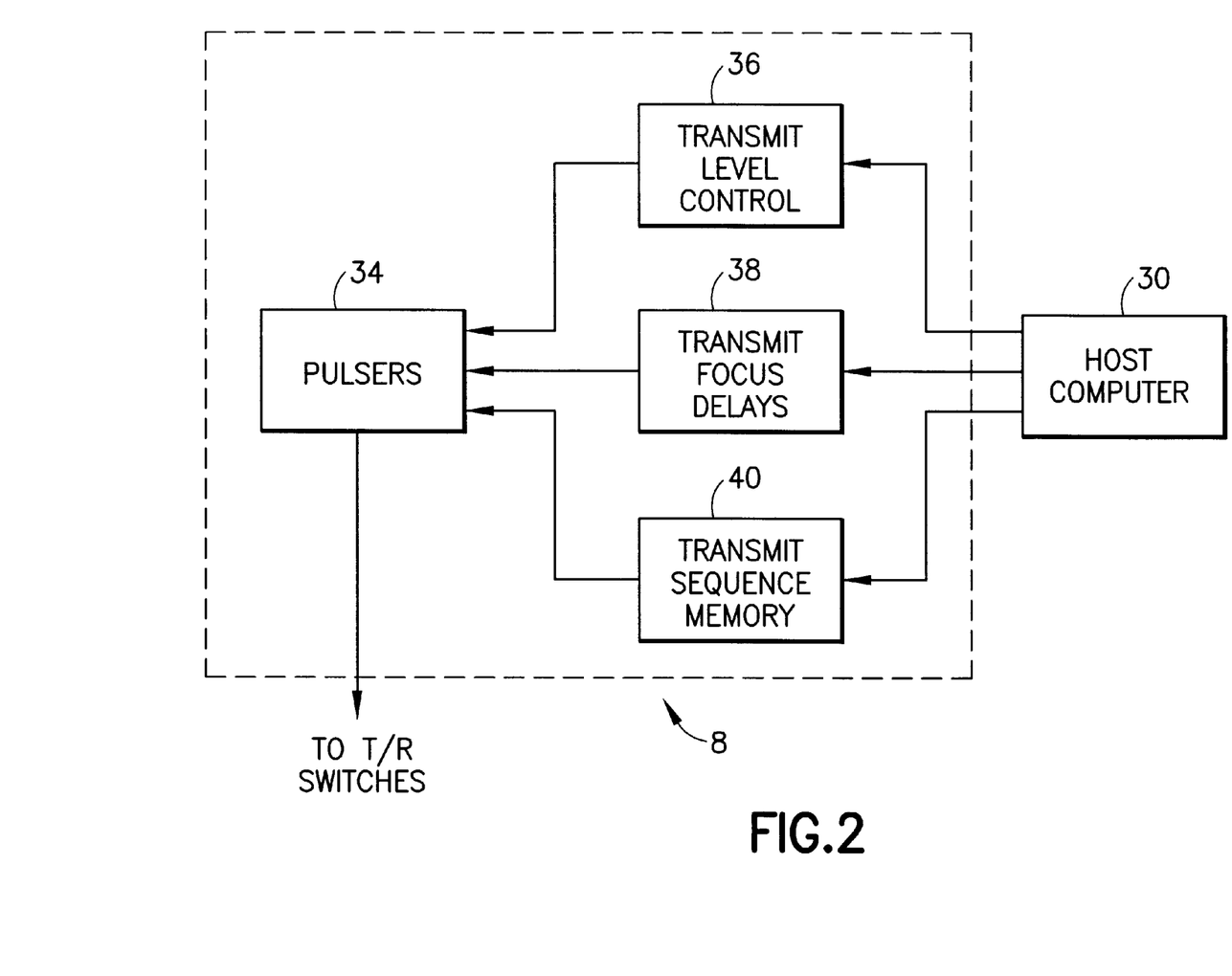
FIG. 2 is a block diagram showing the transmitter incorporated in the system depicted in FIG. 1.

Referring to FIG. 2, adjustment of the transmit waveform frequency and/or length is implemented by programming a digital transmit sequence memory 34.

Each transducer element in the transmit aperture is pulsed by a pulse waveform output by a respective pulser 36 in response to a respective transmit sequence output to that pulser from the transmit sequence memory 34. The frequency and length of each pulse waveform is determined by the respective transmit sequence. For example, if the pulser 36 is bi-polar, +1 and −1 elements of a transmit sequence are transformed into pulses of opposite phase by pulser, while 0 elements correspond to no pulse. The duty cycle or pulse width is proportional to the number of consecutive +1's or −1's in the transmit sequence.

Under the direction of the host computer 30, the transmitter 8 drives the transducer array 2 such that the ultrasonic energy is transmitted as a directed focused beam. To accomplish focusing, respective time delays are imparted to the pulsers 36 by a transmit focus delay block 38, while respective pulse amplitudes are set by transmit level control block 40. The host computer 30 determines the conditions under which the acoustic pulses will be transmitted. With this information, the transmit focus delay and transmit level control blocks will respectively determine the timing and the amplitude of each of the transmit pulses to be generated by the pulsers 36, while the frequency and length of the transmit pulses are determined by the transmit sequences. The host computer can provide different sets of transmit sequences, transmit focus delays and transmit levels for optimal and normal imaging.

Referring again to FIG. 1, the pulsers send the transmit pulses to each of the elements 4 of the transducer array 2 via the T/R switches 6. By appropriately adjusting the transmit focus time delays in a conventional manner, an ultrasonic beam can be directed and focused at a transmit focal zone position. The axial length of the transmit focal zone is a function of the width of the transmit aperture.

Figure 4:
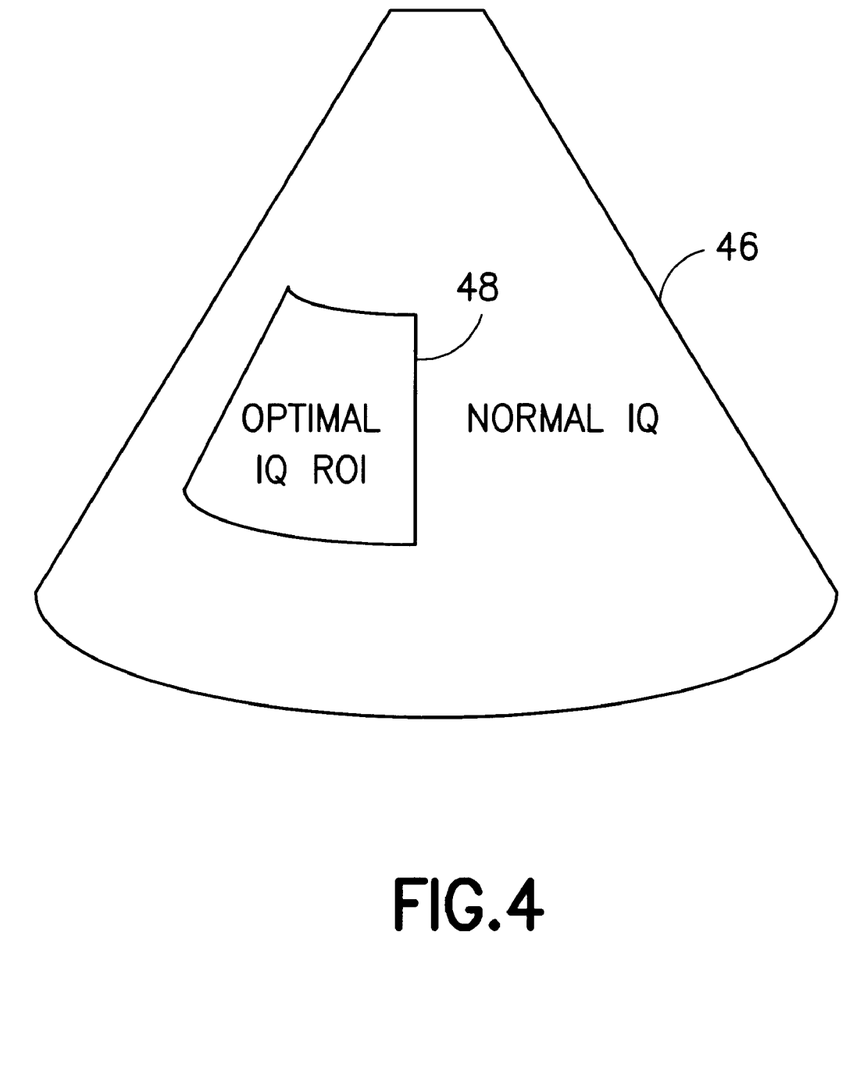
FIG. 4 is a schematic depicting a sector scan in which a ROI image of optimal quality is superimposed on a background image of normal quality in accordance with one preferred embodiment of the invention.

As seen in the sector scan image depicted in FIG. 4, in accordance with one preferred embodiment, the ROI 48 is scanned using a number of focal zones per unit depth which is greater than that used for scanning the background region 46 outside the ROI, i.e., the axial length of the transmit focal zone for optimal imaging of the ROI is less than that for normal imaging of the background region. The carets on the left denote transmit focal zone positions for optimal quality imaging of the ROI; the carets on the right denote transmit focal zone positions for normal quality imaging of the background region. The point being illustrated is simply that the F-numbers and number of focal zones for the ROI can be quite different from the background image.

In accordance with another preferred embodiment, a ROI can be imaged using coded excitation on transmit and pulse compression on receive, while the background is imaged using conventional B-mode imaging (e.g., transmitting an uncoded base waveform and using the demodulator 12 and filter 14 on receive to select a passband centered at the transmit frequency). Coded excitation on transmit is accomplished by convolving a base wave-form with a transmit code sequence to form a coded waveform, which is represented by a coded transmit sequence stored in the transmit sequence memory 34 (see FIG. 2). The beamsummed receive signal for the coded transmit is then pulse compressed by a decoding filter 42, shown in FIG. 3. The decoding filter 42, like the filter 14, receives filter coefficients from a filter coefficient memory 44, which is loaded by the host computer. Preferably the filter coefficients constitute a receive code which matches the transmit code in order to achieve autocorrelation. If the transmit code has n bits, then ideally the amplitude of the pulse-compressed signal can be n times greater than the amplitude of the base waveform. Suitable single-transmit codes are the Barker codes. Barker codes are biphase (or binary) code sequences of various lengths up to n=13. The set of all Barker codes is disclosed in an article by Welch et al. entitled "Sidelobe suppressed spread spectrum pulse compression for ultrasonic tissue imaging," IEEE Trans Ultrasonics, Ferroelec., and Freq. Control (accepted for publication, Aug. 1997).]

Figure 3:
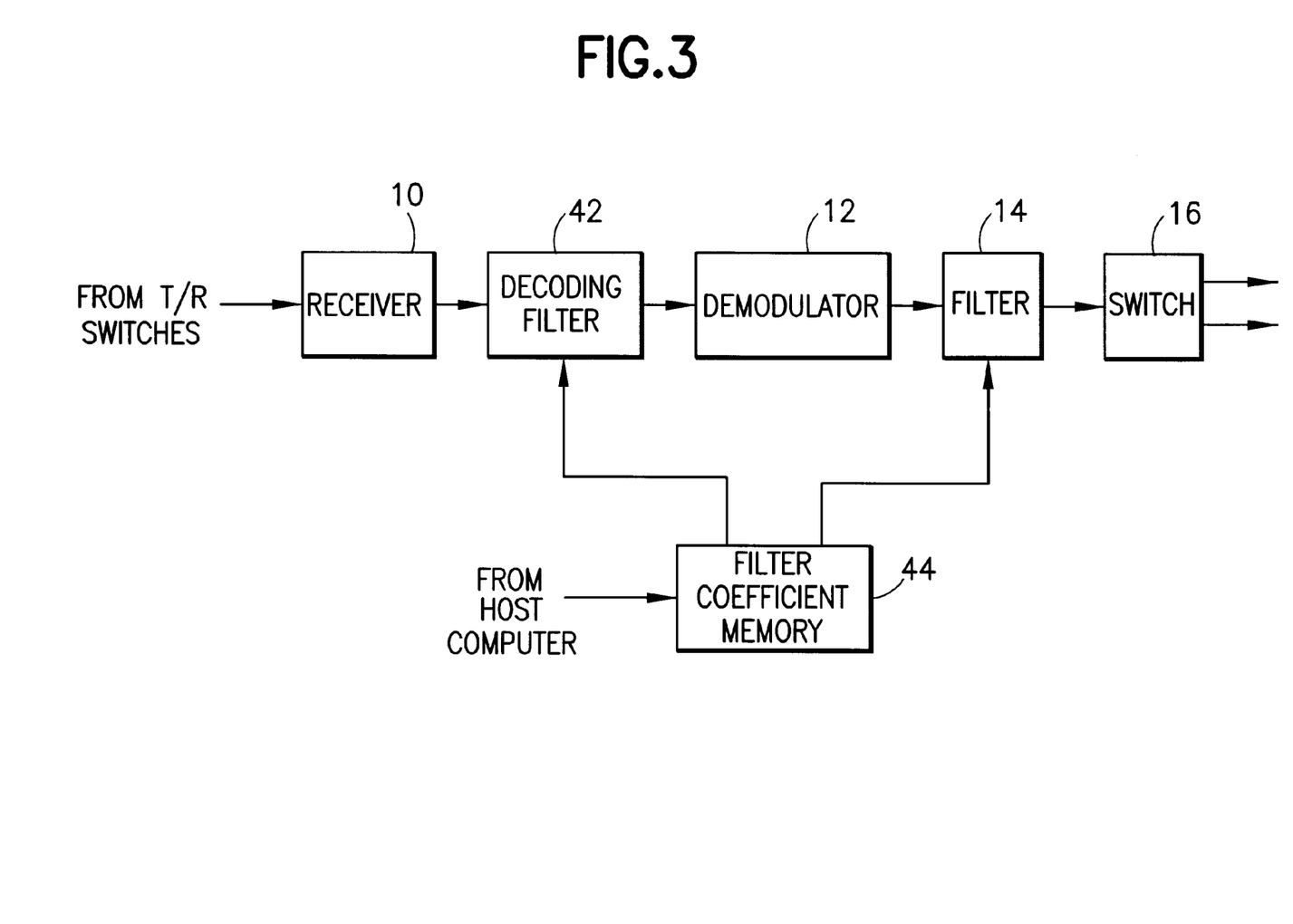
FIG. 3 is a block diagram showing part of an ultrasound imaging system in accordance with another preferred embodiment which employs coded excitation on transmit and pulse compression on receive for optimal imaging of a ROI in the far field.

Alternatively, acceptable sidelobe levels can be produced using a complementary set of transmit codes, e.g., Golay codes, to scan the ROI. This requires two transmit firings per acoustic data sample, both focused at the same transmit focal zone position. A set of complementary-coded waveforms produce signals which, after autocorrelation and summation, yield a short pulse in range, due to the fact that the side-lobe levels produced by the autocorrelation of one code sequence are equal in magnitude but opposite in sign to the those of the complementary sequence. In this case, the decoding filter 42 comprises a correlation filter, which receives first and second sets of filter coefficients from the filter coefficient memory 44, and a vector summer for summing the filtered (partly decoded) signals output by the FIR filter. The first and second sets of filter coefficients represent first and second receive codes which respectively match the first and second complementary transmit codes. After the respective beamsummed receive signals are autocorrelated (partly decoded) by the correlation filter, the partly decoded outputs are summed in the vector summer to form the pulse-compressed (fully decoded) signal. The pulse-compressed receive signal is then demodulated, filtered in filter 14 and channeled by switch 16 to the B-mode processor 18B (see FIG. 1) for envelope detection, logarithmic compression, edge enhancement, etc.

The use of complementary-coded excitation on transmit and pulse compression on receive can be used to acquire a high-quality image of a ROI located in the far field of the full image. Alternatively, orthogonal complementary codes can be used to perform harmonic (or subharmonic) imaging, e.g., in the mid-field of the full image. After autocorrelation, the linear signal components of the two beamsummed receive signals will substantially cancel, leaving nonlinear signal components to be imaged.

The system architecture and processing required to implement optimal-image-quality "picture in a picture" imaging is similar to that for a color flow or power Doppler imaging system in which a color flow image over a user-specified ROI is superposed onto a background B-mode image. Specifically, B-mode "picture in a picture" imaging is similar to color flow in that the ROI imaging parameters, including transmit waveforms, number of transmit focal zones, vector spacing, receive filter coefficients and frame rates are all independent of those for the background B-mode image. Where possible, interleaving of "big picture" vectors and "small picture" vectors should also be used to further maximize the acoustic frame rate. On the other hand, B-mode "picture in a picture" imaging is different from color flow mode in that the "picture in a picture" detection and post-processing algorithms are not fundamentally different from those for the background B-mode imaging, and no threshold logic is needed to decide whether to "write" (store) B-mode amplitude or color flow estimate for the image pixels within the ROI. The position and size of the "picture in a picture" ROI can be adjusted via standard user's interface devices (e.g., a trackball). In accordance with a further variation, it will be appreciated that separate B-mode processors for performing optimal versus normal imaging are not required. A programmable midprocessor may be especially suited for processing the "big picture" and "small picture" vectors either in series or in parallel. In the scan converter, the main requirement is to be able to scan convert the "big picture" and "small picture" frames separately, since their acoustic frame rates can be very different. The incorporation of the "picture in a picture" processing in B-mode imaging should not preclude the concurrent use of color flow imaging, which is based on a separate color ROI.

The foregoing preferred embodiments have been disclosed for the purpose of illustration. Variations and modifications of the concept of the invention will be readily apparent to persons skilled in the art. For example, the "picture in a picture" function is not limited to being implemented in a baseband system, but instead can be implemented in systems in which the RF signal is processed without being demodulated to baseband. A third alternative is to apply a complex bandpass filter on receive to obtain the I/Q components of the fundamental or (sub)harmonic frequency bands for B-mode processing. For pulse compression on receive, the decoding filter can be placed either before or after the demodulator. All such variations and modifications are intended to be encompassed by the claims set forth hereinafter.

What is claimed is:

1. A system for imaging biological tissue, comprising:

a transducer array comprising a multiplicity of transducer elements;

a transmitter programmed in an optimal imaging mode to activate said transducer array to transmit a first multiplicity of ultrasound beams focused in a region of interest during a first scan, and programmed in a normal imaging mode to activate said transducer array to transmit a second multiplicity of ultrasound beams focused in a background region outside of and contiguous with said region of interest during a second scan, wherein said transmitter is programmed to activate said transducer array to transmit coded ultrasound beams during said first scan and to transmit uncoded ultrasound beams during said second scan;

a receiver programmed in said optimal imaging mode to form a respective receive beam of acoustic data from said transducer array for each ultrasound beam focused in said region of interest during said first scan, and programmed in said normal imaging mode to form a respective receive beam of acoustic data from said transducer array for each ultrasound beam focused in said background region during said second scan;

a decoding filter programmed to decode said receive beams of acoustic data for said first scan;

a converter for converting said decoded receive beams of acoustic data of said first scan into a first set of pixel intensity data and converting said receive beams of acoustic data of said second scan into a second set of pixel intensity data; and a display subsystem for displaying a first image portion in a region of interest of a display image and a second image portion in a background region outside of and contiguous with said region of interest of said display image, said first image portion being derived from said first set of pixel intensity data and having a first resolution, and said second image portion being derived from said second set of pixel intensity data and having a second resolution less than said first resolution.

2. A method of imaging biological tissue, comprising the steps of:

transmitting a first multiplicity of ultrasound beams focused in a region of interest during a first scan, wherein said ultrasound beams of said first scan are coded;

acquiring a respective receive beam of acoustic data for each ultrasound beam focused in said region of interest during said first scan;

decoding said receive beams of acoustic data for said first scans;

converting said decoded receive beams of acoustic data of said first scan into a first set of pixel intensity data;

transmitting a second multiplicity of ultrasound beams focused in a background region outside of and contiguous with said region of interest during a second scan, wherein said ultrasound beams of said second scan are uncoded;

acquiring a respective receive beam of acoustic data for each ultrasound beam focused in said back-ground region during said second scan;

converting said receive beams of acoustic data of said second scan into a second set of pixel intensity data; and displaying a first image portion in a region of interest of a display image and a second image portion in a background region outside of and contiguous with said region of interest of said display image, said first image portion being derived from said first set of pixel intensity data and having a first resolution, and said second image portion being derived from said second set of pixel intensity data and having a second resolution less than said first resolution.

3. A system for imaging biological tissue, comprising:

an ultrasound transducer array comprising a multiplicity of transducer elements;

a display monitor for displaying a display image which is a function of pixel intensity data; and a computer programmed to perform the following steps:
  (a) activating transducer elements of said array to transmit a multiplicity of coded ultrasound beams focused in a region of interest during a first scan;
  (b) acquiring a respective receive beam of acoustic data for each ultrasound beam focused in said region of interest during said first scan;
  (c) decoding said receive beams of acoustic data for said first scan;
  (d) converting said decoded receive beams of acoustic data of said first scan into a first set of pixel intensity data;
  (e) activating transducer elements of said array to transmit a multiplicity of uncoded ultrasound beams focused in a background region outside of and contiguous with said region of interest during a second scan;
  (f) acquiring a respective receive beam of acoustic data for each ultrasound beam focused in said background region during said second scan;
  (g) converting said receive beams of acoustic data of said second scan into a second set of pixel intensity data; and
  (h) controlling said display monitor to display a first image portion in a region of interest of a display image and a second image portion in a background region outside of and contiguous with said region of interest of said display image on said display device, said first image portion being derived from said first set of pixel intensity data, and said second image portion being derived from said second set of pixel intensity data.

4. A method of imaging biological tissue, comprising the steps of:

transmitting successive ultrasound beams focused at respective focal zones in a region of interest by activating transducer elements using coded waveforms;

forming a respective beamsummed signal from echo signals returned from said region of interest following each transmission of a coded ultrasound beam;

decoding said beamsummed signals corresponding to said region of interest;

transmitting successive ultrasound beams focused at respective focal zones in a background region outside of said region of interest by activating transducer elements using uncoded waveforms;

forming a respective beamsummed signal from echo signals returned from said background region following each transmission of an uncoded ultrasound beam; and displaying an image frame comprising a first image area representing a first set of image data derived from said decoded beamsummed signals and a second image area representing a second set of image data derived from said beamsummed signals corresponding to said background region.

5. The method as recited in claim 4, wherein each of said coded waveforms is formed by convolving a base waveform with a transmit code.

6. The method as recited in claim 5, wherein said transmit code is a Barker code.

7. The method as recited in claim 5, wherein said decoding step comprises filtering said beamsummed signals corresponding to said region of interest using a receive code which matches said transmit code in order to achieve autocorrelation.

8. The method as recited in claim 4, wherein said decoding step comprises pulse compressing said beamsummed signals corresponding to said region of interest.

9. A method of imaging biological tissue, comprising the steps of:

for each focal zone in a region of interest, transmitting first and second ultrasound beams focused at said respective focal zone by activating transducer elements using first and second coded waveforms respectively, said first and second coded waveforms being encoded with complementary codes;

forming a respective beamsummed signal from echo signals returned from said region of interest following each transmission of a coded ultrasound beam;

decoding said beamsummed signals corresponding to said region of interest;

transmitting successive ultrasound beams focused at respective focal zones in a background region outside of said region of interest by activating transducer elements using uncoded waveforms;

forming a respective beamsummed signal from echo signals returned from said background region following each transmission of an uncoded ultrasound beam; and displaying an image frame comprising a first image area representing a first set of image data derived from said decoded beamsummed signals and a second image area representing a second set of image data derived from said beamsummed signals corresponding to said background region.

10. The method as recited in claim 9, wherein each of said first coded waveforms is formed by convolving a base waveform with a first transmit code and each of said second coded waveforms is formed by convolving a base waveform with a second transmit code.

11. The method as recited in claim 10, wherein said first and second transmit codes are Golay codes.

12. The method as recited in claim 9, wherein said decoding step comprises the steps of:

filtering said beamsummed signals corresponding to said region of interest using first and second receive codes which respectively match said first and second transmit codes in order to achieve autocorrelation; and for each set of transmits to a particular focal zone, vector summing said filtered beamsummed signals.

13. A system for imaging biological tissue, comprising:
an ultrasound transducer array comprising a multiplicity of transducer elements;
a display monitor for displaying an image frame; and
a computer programmed to perform the following steps:
(a) using coded waveforms to activate transducer elements of said array to transmit successive ultrasound beams focused at respective focal zones in a region of interest;
(b) forming a respective beamsummed signal from echo signals returned from said region of interest following each transmission of a coded ultrasound beam;
(c) decoding said beamsummed signals corresponding to said region of interest;
(d) using uncoded waveforms to activate transducer elements of said array to transmit successive ultrasound beams focused at respective focal zones in a background region outside of said region of interest;
(e) forming a respective beamsummed signal from echo signals returned from said background region following each transmission of an uncoded ultrasound beam; and
(f) controlling said display monitor to display an image frame comprising a first image area representing a first set of image data derived from said decoded beamsummed signals and a second image area representing a second set of image data derived from said beamsummed signals corresponding to said background region.

14. The system as recited in claim 13, wherein each of said coded waveforms is formed by convolving a base waveform with a transmit code.

15. The system as recited in claim 14, wherein said transmit code is a Barker code.

16. The system as recited in claim 13, wherein said decoding step comprises pulse compressing said beamsummed signals corresponding to said region of interest.

17. The system as recited in claim 16, wherein said decoding step comprises filtering said beamsummed signals corresponding to said region of interest using a receive code which matches said transmit code in order to achieve autocorrelation.

18. A system for imaging biological tissue, comprising:
an ultrasound transducer array comprising a multiplicity of transducer elements;
a display monitor for displaying an image frame; and
a computer programmed to perform the following steps:
(a) for each focal zone in a region of interest, using first and second coded waveforms to activate transducer elements of said array to transmit first and second ultrasound beams focused at said respective focal zone, said first and second coded waveforms being encoded with complementary codes;
(b) forming a respective beamsummed signal from echo signals returned from said region of interest following each transmission of a coded ultrasound beam;
(c) decoding said beamsummed signals corresponding to said region of interest;
(d) using uncoded waveforms to activate transducer elements of said array to transmit successive ultrasound beams focused at respective focal zones in a background region outside of said region of interest;
(e) forming a respective beamsummed signal from echo signals returned from said background region following each transmission of an uncoded ultrasound beam; and (f) controlling said display monitor to display an image frame comprising a first image area representing a first set of image data derived from said decoded beamsummed signals and a second image area representing a second set of image data derived from said beamsummed signals corresponding to said background region.

19. The system as recited in claim 18, wherein each of said first coded waveforms is formed by convolving a base waveform with a first transmit code and each of said second coded waveforms is formed by convolving a base waveform with a second transmit code.

20. The system as recited in claim 19, wherein said first and second transmit codes are Golay codes.

21. The system as recited in claim 18, wherein said decoding step comprises the steps of:

filtering said beamsummed signals corresponding to said region of interest using first and second receive codes which respectively match said first and second transmit codes in order to achieve autocorrelation; and for each set of transmits to a particular focal zone, vector summing said filtered beamsummed signals.

* * * * *